United States Patent
Kasai et al.

(10) Patent No.: US 12,222,344 B2
(45) Date of Patent: Feb. 11, 2025

(54) METHOD FOR USING LUBRICATING OIL COMPOSITION AND METHOD FOR EVALUATING DEGRADATION

(71) Applicant: Idemitsu Kosan Co., Ltd., Chiyoda-ku (JP)

(72) Inventors: Moritsugu Kasai, Tokyo (JP); Tatsuya Kusumoto, Tokyo (JP)

(73) Assignee: Idemitsu Kosan Co., Ltd., Chiyoda-ku (JP)

( * ) Notice: Subject to any disclaimer, the term of this patent is extended or adjusted under 35 U.S.C. 154(b) by 287 days.

(21) Appl. No.: 17/759,057

(22) PCT Filed: Jan. 20, 2021

(86) PCT No.: PCT/JP2021/001775
§ 371 (c)(1),
(2) Date: Jul. 19, 2022

(87) PCT Pub. No.: WO2021/149701
PCT Pub. Date: Jul. 29, 2021

(65) Prior Publication Data
US 2023/0057229 A1 Feb. 23, 2023

(30) Foreign Application Priority Data
Jan. 21, 2020 (JP) .................. 2020-007666

(51) Int. Cl.
*G01N 33/28* (2006.01)
*C10M 125/22* (2006.01)
(Continued)

(52) U.S. Cl.
CPC ....... *G01N 33/2888* (2013.01); *C10M 125/22* (2013.01); *C10M 129/52* (2013.01);
(Continued)

(58) Field of Classification Search
CPC ... G01N 33/2888; G01N 33/30; C10M 25/22; C10M 129/52; C10M 129/54;
(Continued)

(56) References Cited

U.S. PATENT DOCUMENTS

| | | |
|---|---|---|
| 2009/0216471 A1 | 8/2009 | Akiyama et al. |
| 2012/0229151 A1 | 9/2012 | Katafuchi |
| 2012/0229152 A1 | 9/2012 | Katafuchi |

FOREIGN PATENT DOCUMENTS

| | | |
|---|---|---|
| JP | 63-103961 A | 5/1998 |
| JP | 2003-11 4206 A | 4/2003 |

(Continued)

OTHER PUBLICATIONS

International Search Report mailed on Mar. 30, 2021 in PCT/JP2021/001775 filed on Jan. 21, 2021 (3 pages).

*Primary Examiner* — Jamel E Williams
(74) *Attorney, Agent, or Firm* — Oblon, McClelland, Maier & Neustadt, L.L.P.

(57) ABSTRACT

A method for utilizing a lubricating oil composition in which the content of a metal-based cleaning agent (X) having a base value of 100 mgKOH/g or less is 630 mass ppm or less in terms of metal atoms, and the content of sulfated ash is 1.5 mass % or less. The method includes measuring at least one physical property value among the capacitance and the dielectric constant of the lubricating oil composition while using the lubricating oil composition, and evaluating the progress of degradation of the lubricating oil composition.

7 Claims, 2 Drawing Sheets

(51) Int. Cl.
  *C10M 129/52*      (2006.01)
  *C10M 129/54*      (2006.01)
  *C10M 169/04*      (2006.01)
  *G01N 33/30*       (2006.01)
  *C10N 10/04*       (2006.01)
  *C10N 30/00*       (2006.01)
  *C10N 30/04*       (2006.01)

(52) U.S. Cl.
  CPC ........ *C10M 129/54* (2013.01); *C10M 169/04* (2013.01); *G01N 33/30* (2013.01); *C10M 2201/084* (2013.01); *C10M 2207/142* (2013.01); *C10M 2207/144* (2013.01); *C10N 2010/04* (2013.01); *C10N 2030/04* (2013.01); *C10N 2030/52* (2020.05)

(58) Field of Classification Search
  CPC ...... C10M 2201/084; C10M 2207/142; C10M 2207/144; C10N 2030/52; C10N 2010/04; C10N 2030/04
  See application file for complete search history.

(56) References Cited

FOREIGN PATENT DOCUMENTS

| | | |
|---|---|---|
| JP | 2009-2887 A | 1/2009 |
| JP | 2009-198341 A | 9/2009 |
| JP | 2011-80814 A | 4/2011 |
| JP | 2012-83254 A | 4/2012 |
| JP | 2017-219420 A | 12/2017 |
| WO | WO 2011/065340 A1 | 6/2011 |
| WO | WO-2011065339 A1 * | 6/2011 ........... G01N 27/414 |

* cited by examiner

METHOD FOR USING LUBRICATING OIL COMPOSITION AND METHOD FOR EVALUATING DEGRADATION

CROSS REFERENCE TO RELATED APPLICATIONS

This application is a continuation application of PCT/JP2021/001775, filed on Jan. 20, 2021, and claims priority to Japanese Patent Application No. 2020-007666, filed on Jan. 21, 2020, the entire contents of which are incorporated herein by reference.

TECHNICAL FIELD

The present invention relates to a method for using a lubricating oil composition, a method for evaluating degradation of a lubricating oil composition, and a lubricating oil composition and a measurement apparatus used in these methods.

BACKGROUND ART

As degradation of lubricating oil compositions used in various applications progresses due to their use in lubricating various components or else, it may have a significant adverse effect on the performance and durability of machines and equipment using the lubricating oil compositions, and further on the energy saving performance. The rate of progress of degradation of a lubricating oil composition varies depending greatly on the environment in which the composition is used. Therefore, a means for accurately evaluating the progress of degradation of a lubricating oil composition under various operating environments has been studied.

For example, Patent literature 1 discloses a technique relating to a device for detecting degradation of a lubricating oil for machine tools, the device comprising a judgment means which measures the conductivity and dielectric constant of the lubricating oil and determines the degradation of the lubricating oil from these measured values.

CITATION LIST

Patent Literature

Patent literature 1: JP-A-2011-80814

SUMMARY OF INVENTION

Technical Problem

Under these circumstances, there has been a need for a method for more accurately evaluating the progress of degradation of lubricating oil compositions used in various applications.

Solution to Problem

The present invention provides a method for using a lubricating oil composition and a method for evaluating degradation of a lubricating oil composition, where, in the lubricating oil composition, the content of a metal-based detergent (in terms of metal atoms) having a prescribed base number or less and the content of sulfated ash are adjusted to be less than or equal to prescribed values.

Specific aspects of the present invention are as described in [1] to [7] below.

[1] A method for using a lubricating oil composition in which the content of a metal-based detergent (X) having a base number of 100 mgKOH/g or less is 630 mass ppm or less in terms of metal atoms and the content of sulfated ash is 1.5 mass % or less, the method comprising a step of measuring a value of at least one physical property among the electrostatic capacity and dielectric constant of the lubricating oil composition while the lubricating oil composition is in use to evaluate the progress of degradation of the lubricating oil composition.

[2] A method for evaluating degradation of a lubricating oil composition in which the content of a metal-based detergent (X) having a base number of 100 mgKOH/g or less is 630 mass ppm or less in terms of metal atoms and the content of sulfated ash is 1.5 mass % or less, the method comprising a step of measuring a value of at least one physical property among the electrostatic capacity and dielectric constant of the lubricating oil composition to evaluate the progress of degradation of the lubricating oil composition.

[3] The method for evaluating degradation of a lubricating oil composition according to [2] above, wherein the measurement is performed at any point in time or continuously while the lubricating oil composition is in use to evaluate the progress of degradation of the lubricating oil composition.

[4] A lubricating oil composition in which the content of a metal-based detergent (X) having a base number of 100 mgKOH/g or less is 630 mass ppm or less in terms of metal atoms and the content of sulfated ash is 1.5 mass % or less, wherein the degraded state of the lubricating oil composition is presented by measuring at least one of the electrostatic capacity and dielectric constant thereof.

[5] The lubricating oil composition according to [4] above, wherein when the lubricating oil composition is continuously used immediately from the start of use, at least one of the electrostatic capacity and dielectric constant of the lubricating oil composition increases with time from the start of use.

[6] An apparatus for measuring a value of at least one physical property among the electrostatic capacity and dielectric constant of a lubricating oil composition in which the content of a metal-based detergent (X) having a base number of 100 mgKOH/g or less is 630 mass ppm or less in terms of metal atoms and the content of sulfated ash is 1.5 mass % or less, the apparatus comprising:

a measurement unit for measuring the value of the physical property at a predetermined point in time; and a recording section for recording the value of the physical property measured by the measurement unit.

[7] The measurement apparatus according to [6] above, further comprising an evaluation section for evaluating the progress of degradation of the lubricating oil composition based on the value of the physical property recorded in the recording section.

Advantageous Effects of Invention

A method for using a lubricating oil composition and a method for evaluating degradation of a lubricating oil composition according to preferred aspects of the invention are capable of determining the progress of degradation of a lubricating oil composition used in various applications in a more accurate, more rapid, and more convenient manner.

DESCRIPTION OF EMBODIMENTS

[Constitution of Lubricating Oil Composition]

First, a lubricating oil composition which is used in a method for using the same and a method for evaluating degradation of the same will be described.

In a lubricating oil composition used in the present invention, the content of a metal-based detergent (X) having a base number of 100 mgKOH/g or less is 630 mass ppm or less in terms of metal atoms and the content of sulfated ash is 1.5 mass % or less. The lubricating oil composition is characterized in that the degraded state thereof can easily be determined by measuring at least one of the electrostatic capacity and dielectric constant thereof.

In general, the degree of progress of degradation of a lubricating oil composition can be evaluated, for example, by a ratio of a base number of a degraded oil to a base number of a new oil [degraded oil/new oil]. Specifically, the smaller the value of ratio [degraded oil/new oil], the more the degradation is evaluated to have been progressed. However, it is difficult to measure the ratio [degraded oil/new oil], for example, continuously and continually while the lubricating oil composition is in use. Thus, a more accurate, more rapid, and more convenient method for determining the progress of degradation of a lubricating oil composition had been required.

As the ratio of the base number of the degraded oil to the base number of the new oil [degraded oil/new oil] becomes smaller and the degradation of the lubricating oil composition progresses, the electrostatic capacity and dielectric constant of the lubricating oil composition generally tend to increase. However, in some cases, even during the progress of degradation of the lubricating oil composition, the values of the electrostatic capacity and dielectric constant were found to temporarily decrease or remain unchanged for a certain period of time. Due to such a tendency, even if the electrostatic capacity or dielectric constant is measured to evaluate the progress of degradation of the lubricating oil composition at any given point in time, these values may not be reliable to accurately determine the progress of degradation of the lubricating oil composition, considering that the above case may occur.

The present inventors have investigated various factors that may cause a temporary decrease in the values of the electrostatic capacity and dielectric constant of a lubricating oil composition. As a result, it was found that a temporary decrease in the values of electrostatic capacity and dielectric constant is likely to occur despite the progress of the degradation and that inconsistent correlation may occur between the values of the electrostatic capacity and dielectric constant and the degradation of the lubricating oil composition when the content of a metal-based compound, i.e., the content of sulfated ash, or the content of a metal-based detergent (X) having a base number of 100 mgKOH/g or less, in the lubricating oil composition is more than or equal to a prescribed value.

Based on these findings, a lubricating oil composition used in the present invention is adjusted such that the content of a metal-based detergent (X) having a base number of 100 mgKOH/g or less is 630 mass ppm or less in terms of metal atoms, and the content of sulfated ash is 1.5 mass % or less.

From the above point of view, in a lubricating oil composition used in the present invention, the content of a metal-based detergent (X) is 630 mass ppm or less in terms of metal atoms relative to the total amount (100 mass %) of the lubricating oil composition, or it may be 610 mass ppm or less, 605 mass ppm or less, 550 mass ppm or less, 500 mass ppm or less, 450 mass ppm or less, or 420 mass ppm or less.

The lower limit of the content of the metal-based detergent (X) in terms of metal atoms can be determined as desired as long as the upper limit is adjusted to be in the above range. For example, the lower limit may be 0 mass ppm or more, 1 mass ppm or more, 5 mass ppm or more, 10 mass ppm or more, 50 mass ppm or more, or 100 mass ppm or more relative to the total amount (100 mass %) of the lubricating oil composition.

The range of the content of the metal-based detergent (X) in terms of metal atoms can be specified by appropriately selecting from the options for the upper and lower limits mentioned above in any combination.

Herein, the contents of a metal-based detergent (X) and a metal-based detergent (Y) described below in terms of metal atoms can be measured using a measurement apparatus for LC-MS (high performance liquid chromatograph-mass spectrometer), infrared spectroscopy, ICP atomic emission spectrometry, or the like, on a measurement sample obtained after separating and removing additives in the lubricating oil composition in a pretreatment. For example, they can be measured in accordance with JPI-5S-38-92.

While the base number of a metal-based detergent (X) should be 100 mgKOH/g or less, it may also be 90 mgKOH/g or less, 80 mgKOH/g or less, 70 mgKOH/g or less, 60 mgKOH/g or less, 50 mgKOH/g or less, 40 mgKOH/g or less, 30 mgKOH/g or less, 20 mgKOH/g or less, or 10 mgKOH/g or less, and may be 0 mgKOH/g or more, 1 mgKOH/g or more, 5 mgKOH/g or more, or 10 mgKOH/g or more.

A "base number" as used herein refers to a base number measured in accordance with the perchloric acid method described in section "7." of JIS K2501 "Petroleum products and lubricants—Determination of neutralization number".

From the above point of view, in the lubricating oil composition used in the present invention, the content of sulfated ash is preferably 1.4 mass % or less, and more preferably 1.3 mass % or less, relative to the total amount (100 mass %) of the lubricating oil composition.

The lower limit of the content of the sulfated ash is determined as desired according to the application of the lubricating oil composition. In a lubricating oil composition according to one aspect of the present invention, the content of sulfated ash may be 0.01 mass % or more, 0.03 mass % or more, 0.05 mass % or more, or 0.1% or more, relative to the total amount (100 mass %) of the lubricating oil composition.

The range of the content of the sulfated ash can be specified by appropriately selecting from the options for the upper and lower limits mentioned above in any combination.

Herein, a content of sulfated ash refers to a value measured in accordance with JIS K2272:1998.

A lubricating oil composition used in one aspect of the present invention can contain a base oil and various additives selected as appropriate for the application, as long as the aforementioned contents of the metal-based detergent (X) and sulfated ash are adjusted to be in the above-mentioned ranges.

Hereinafter, each component that may be contained in a lubricating oil composition used in one aspect of the invention will be described.

<Base Oil>

Examples of a base oil contained in a lubricating oil composition used in one aspect of the present invention include one or more kinds selected from mineral oils and synthetic oils.

Examples of the mineral oils include atmospheric residues obtained by subjecting crude oils, such as paraffinic crude oil, intermediate base crude oil, and naphthenic crude oil, to atmospheric distillation; distillates obtained by subjecting these atmospheric residues to vacuum distillation; and refined oils obtained by subjecting the distillates to one or more refining treatments among solvent deasphalting, solvent extraction, hydrocracking, solvent dewaxing, catalytic dewaxing, and hydrorefining.

Examples of the synthetic oils include poly-α-olefins, such as an α-olefin homopolymer and an α-olefin copolymer (for example, an α-olefin copolymer having 8 to 14 carbon atoms such as an ethylene-α-olefin copolymer); isoparaffin; polyalkylene glycol; ester oils, such as polyol ester, dibasic acid ester, and phosphoric acid ester; ether oils, such as polyphenyl ether; alkylbenzene; alkylnaphthalene; and synthetic oil (GTL) obtained by isomerizing wax (GTL WAX (Gas To Liquids WAX)) produced from natural gas through Fischer-Tropsch process or the like.

Among these, it is preferable that the base oil used in one aspect of the present invention includes one or more kinds selected from the mineral oils classified in Group II or Group III of the API (American Petroleum Institute) base oil category, and synthetic oils.

While the kinematic viscosity of the base oil used in one aspect of the present invention at 100° C. can suitably be determined according to the application of the lubricating oil composition, it is preferably 2 to 20 mm²/s, more preferably 2 to 15 mm²/s, and still more preferably 3 to 12 mm²/s.

While the viscosity index of the base oil used in one aspect of the present invention can suitably be determined according to the application of the lubricating oil composition, it is preferably 70 or more, more preferably 80 or more, still more preferably 90 or more, and yet still more preferably 100 or more.

When a mixed oil, i.e., a combination of two or more kinds of base oils, is used as the base oil in one aspect of the present invention, the kinematic viscosity and the viscosity index of the mixed oil are preferably in the above ranges.

In the lubricating oil composition in one aspect of the present invention, the content of the base oil is preferably 30 to 99.99 mass %, more preferably 50 to 99.9 mass %, and still more preferably 65 to 98.0 mass %, relative to the total amount (100 mass %) of the lubricating oil composition.

<Metal-Based Detergent>

The lubricating oil composition used in one aspect of the invention preferably contains a metal-based detergent.

For example, when the lubricating oil composition is used as an engine oil, it can effectively suppress generation of sludge or the like.

The metal-based detergent used in one aspect of the invention may be used alone or in combination of two or more kinds.

A metal atom composing the metal-based detergent used in one aspect of the invention is preferably an alkali metal atom or an alkaline earth metal atom, more preferably calcium, magnesium, or barium, and still more preferably calcium.

Examples of the metal-based detergent used in one aspect of the invention include metal salicylates, metal sulfonates, and metal phenates. The metal salicylates are preferably compounds represented by the following general formula (a-1), the metal sulfonates are preferably compounds represented by the following general formula (a-2), and the metal phenates are preferably compounds represented by the following general formula (a-3).

In the above general formulae (a-1) to (a-3), M is a metal atom and p is the valence of the metal atom M. This metal atom is preferably an alkali metal atom or an alkaline earth metal atom, more preferably calcium, magnesium, or barium, and still more preferably calcium.

R are each independently a hydrogen atom or a hydrocarbon group having 1 to 18 carbon atoms.

Examples of the hydrocarbon groups that can be selected as R include an alkyl group having 1 to 18 carbon atoms, an alkenyl group having 1 to 18 carbon atoms, a cycloalkyl group having 3 to 18 ring-forming carbon atoms, an aryl group having 6 to 18 ring-forming carbon atoms, an alkylaryl group having 7 to 18 carbon atoms, and an arylalkyl group having 7 to 18 carbon atoms.

In the above general formula (a-3), Y is an integer of 0 or more, and preferably an integer of 0 to 3.

As mentioned above, the lubricating oil composition used in one aspect of the present invention is limited in the content of the metal-based detergent (X), but the lubricating oil composition may contain a metal-based detergent (Y) having a base number exceeding 100 mgKOH/g to the extent that the effect of the invention is not impaired. For example, when the lubricating oil composition is used as an engine oil, it can effectively suppress generation of sludge or the like by containing the metal-based detergent (Y).

In the lubricating oil composition used in one aspect of the present invention, the content of the metal-based detergent (Y) in terms of metal atoms is preferably 100 to 6,000 mass ppm, more preferably 100 to 5,000 mass ppm, still more preferably 100 to 4,000 mass ppm, and yet still more preferably 100 to 3,500 mass ppm, relative to the total amount (100 mass %) of the lubricating oil composition.

In the lubricating oil composition used in one aspect of the present invention, the ratio [(X)/(Y)], i.e., the mass content of the metal-based detergent (X) to the mass content of the metal-based detergent (Y) in terms of metal atoms, is preferably 1.0 or less, more preferably 0.5 or less, and still more preferably 0.3 or less.

While the lower limit of this content ratio [(X)/(Y)] is not particularly limited, and may be determined suitably according to the application, it may be, for example, 0 or more, 0.0001 or more, 0.0005 or more, 0.001 or more, 0.005 or more, 0.01 or more, 0.03 or more, 0.05 or more, or 0.07 or more.

The range of the content ratio [(X)/(Y)] can be specified by appropriately selecting the lower limit from those mentioned above in any combination with the upper limit of the preferred aspect mentioned above.

Herein, the metal-based detergent (Y) is defined as a metal-based detergent having a base number exceeding 100 mgKOH/g, and is distinguished from the aforementioned metal-based detergent (X) by the range of their base numbers.

The base number of the metal-based detergent (Y) may also be 120 mgKOH/g or more, 150 mgKOH/g or more, 170 mgKOH/g or more, 200 mgKOH/g or more, 230 mgKOH/g or more, 250 mgKOH/g or more, 270 mgKOH/g or more, 300 mgKOH/g or more, or 320 mgKOH/g or more, and at the same time, 600 mgKOH/g or less, 550 mgKOH/g or less, 500 mgKOH/g or less, 470 mgKOH/g or less, 450 mgKOH/g or less, 420 mgKOH/g or less, 400 mgKOH/g or less, or 380 mgKOH/g or less.

The range of the base number of the metal-based detergent (Y) can be specified by appropriately selecting from the options for the upper and lower limits mentioned above in any combination.

In a lubricating oil composition in one aspect of the present invention, the sum content of the metal-based detergents (X) and (Y) in terms of metal atoms is appropriately adjusted such that the content of the sulfated ash is within the range described above, where the sum content is preferably 0.01 to 0.6 mass %, more preferably 0.01 to 0.5 mass %, still more preferably 0.01 to 0.4 mass %, and yet still more preferably 0.01 to 0.35 mass % relative to the total amount (100 mass %) of the lubricating oil composition.

<Ashless Dispersant>

The lubricating oil composition used in one aspect of the invention may contain an ashless dispersant. The inclusion of the ashless dispersant allows uniform dispersion of additives including the metal-based detergent described above.

The ashless dispersant may be used alone or in combination of two or more kinds.

In a lubricating oil composition used in one aspect of the present invention, the content of an ashless dispersant is suitably determined according to the application, but it is preferably 0.10 to 15.0 mass %, more preferably 0.50 to 12.0 mass %, still more preferably 1.0 to 10.0 mass %, and yet still more preferably 2.5 to 8.0 mass %, relative to the total amount (100 mass %) of the lubricating oil composition.

While examples of the ashless dispersant used in one aspect of the invention include succinimides, benzylamines, succinic acid esters, and boron-modified products thereof, it is preferably one or more selected from non-boron-modified alkenyl succinimides and boron-modified alkenyl succinimides (hereinafter, these two are also collectively called "alkenyl succinimides"), and more preferably a combination of a non-boron-modified alkenyl succinimide and a boron-modified alkenyl succinimide.

Examples of the non-boron-modified alkenyl succinimide used in one aspect of the present invention include an alkenyl bis-succinimide represented by the following general formula (b-1) and an alkenyl monosuccinimide represented by the following general formula (b-2).

In the above general formulae (b-1) and (b-2), $R^{A1}$, $R^{A2}$ and $R^{A3}$ are each independently an alkenyl group having a mass-average molecular weight (Mw) of 500 to 3,000 (preferably 900 to 2,500).

Examples of the alkenyl groups that can be selected as $R^{A1}$, $R^{A2}$ and $R^{A3}$ include a polybutenyl group, a polyisobutenyl group, and an ethylene-propylene copolymer. Among these, a polybutenyl group or a polyisobutenyl group is preferable.

$R^{B1}$, $R^{B2}$ and $R^{B3}$ are each independently an alkylene group having 2 to 5 carbon atoms.

x1 is an integer of 0 to 10, preferably an integer of 1 to 4, and more preferably 2 or 3.

x2 is an integer of 1 to 10, preferably an integer of 2 to 5, and more preferably 3 or 4.

Furthermore, while the boron-modified alkenyl succinimide used in one aspect of the present invention may be, for example, a boron-modified product of an alkenyl bis-succinimide represented by the aforementioned general formula (b-1) and a boron-modified product of an alkenyl monosuccinimide represented by the aforementioned general formula (b-2), it is preferably a boron-modified product of an alkenyl monosuccinimide represented by the aforementioned general formula (b-2).

In one aspect of the present invention, the ratio [B/N] of boron atoms to nitrogen atoms, both atoms constituting the boron-modified alkenyl succinimide, is preferably 0.1 or more, more preferably 0.3 or more, still more preferably 0.5 or more, yet still more preferably 0.7 or more, and particularly preferably 0.9 or more.

Herein, the content of boron atoms refers to the value measured in accordance with JPI-5S-38-92. In addition, the content of nitrogen atoms refers a value measured in accordance with JIS K2609:1998.

In one aspect of the present invention, the ratio [B/N] of the content of boron atoms derived from boron-modified alkenyl succinimide to the content of nitrogen atoms derived from alkenyl succinimide (non-boron-modified alkenyl succinimide and boron-modified alkenyl succinimide) by mass is preferably 0.01 to 0.60, more preferably 0.05 to 0.50, still more preferably 0.10 to 0.45, yet still more preferably 0.15 to 0.40, and particularly preferably 0.20 to 0.35.

In a lubricating oil composition used in one aspect of the present invention, the content of alkenyl succinimide in terms of nitrogen atoms is preferably 0.005 to 0.30 mass %, more preferably 0.01 to 0.20%, still more preferably 0.02 to 0.15 mass %, and yet still more preferably 0.04 to 0.10%, relative to the total amount (100 mass %) of the lubricating oil composition.

In a lubricating oil composition used in one aspect of the invention, the content of boron atoms derived from the boron-modified alkenyl succinimide is preferably 0.20 mass % or less, more preferably 0.18 mass % or less, still more preferably 0.10 mass % or less, and yet still more preferably 0.05 mass % or less, relative to the total amount (100 mass %) of the lubricating oil composition.

<Anti-Wear Agent>

If a lubricating oil composition used in one aspect of the invention is used, for example, as an engine oil or the like, it may contain an anti-wear agent. The anti-wear agent may be used alone or in combination of two or more kinds.

In a lubricating oil composition used in one aspect of the present invention, the content of the anti-wear agent may be suitably determined according to the application, but it is preferably 0.01 to 3.0 mass %, more preferably 0.05 to 2.5 mass %, still more preferably 0.10 to 2.0 mass %, and yet still more preferably 0.20 to 1.5 mass %, relative to the total amount (100 mass %) of the lubricating oil composition.

When a phosphorus-containing anti-wear agent is used as an anti-wear agent in a lubricating oil composition used in one aspect of the present invention, the content of the phosphorus-containing anti-wear agent in terms of phosphorus atoms is preferably 0.005 to 0.20 mass %, more preferably 0.010 to 0.15 mass %, still more preferably 0.015 to 0.10 mass %, and yet still more preferably 0.020 to 0.08 mass %, relative to the total amount (100 mass %) of the lubricating oil composition.

When a sulfur-containing anti-wear agent is used as an anti-wear agent in a lubricating oil composition used in one aspect of the present invention, the content of the sulfur-containing anti-wear agent in terms of sulfur atoms is preferably 0.02 to 0.60 mass %, more preferably 0.03 to 0.50 mass %, still more preferably 0.04 to 0.40 mass %, and yet still more preferably 0.05 to 0.30 mass %, relative to the total amount (100 mass %) of the lubricating oil composition.

Herein, the content of phosphorus atoms refers to the value measured in accordance with JPI-5S-38-92. In addition, the content of sulfur atoms refers to the value measured in accordance with JIS K2541-6:2013.

Examples of the anti-wear agent used in one aspect of the invention include sulfur-containing compounds such as zinc dialkyldithiophosphate (ZnDTP), zinc phosphate, zinc dithiocarbamate, molybdenum dithiocarbamate, molybdenum dithiophosphate, disulfides, sulfurized olefins, sulfurized fats and oils, sulfurized esters, thiocarbonates, thiocarbamates, and polysulfides; phosphorus-containing compounds such as phosphite esters, phosphate esters, phosphonate esters, and amine salts or metal salts thereof; sulfur- and phosphorus-containing anti-wear agents such as thiophosphate esters, thiophosphate esters, thiophosphonate esters, and amine salts or metal salts thereof.

Among these, zinc dialkyldithiophosphate (ZnDTP) is preferably contained in the anti-wear agent used in one aspect of the invention. Examples of zinc dithiophosphate include compounds represented by the following general formula (c-1).

(c-1)

In the above general formula (c-1), $R^1$ to $R^4$ each independently represent a hydrocarbon group, and may be the same as one another or may be different from one another.

The number of carbon atoms of the hydrocarbon group that can be selected as $R^1$ to $R^4$ is preferably 1 to 20, more preferably 1 to 16, still more preferably 3 to 12, and yet still more preferably 3 to 10.

Specific examples of the hydrocarbon groups that can be selected as $R^1$ to $R^4$ include alkyl groups, such as a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, and an octadecyl group; alkenyl groups, such as an octenyl group, a nonenyl group, a decenyl group, a undecenyl group, a dodecenyl group, a tridecenyl group, a tetradecenyl group, and a pentadecenyl group; cycloalkyl groups, such as a cyclohexyl group, a dimethylcyclohexyl group, an ethylcyclohexyl group, a methylcyclohexylmethyl group, a cyclohexylethyl group, a propylcyclohexyl group, a butylcyclohexyl group, and a heptylcyclohexyl group; aryl groups, such as a phenyl group, a naphthyl group, an anthracenyl group, a biphenyl group, and a terphenyl group; alkylaryl groups, such as a tolyl group, a dimethylphenyl group, a butylphenyl group, a nonylphenyl group, a methylbenzyl group, and a dimethylnaphthyl group; and arylalkyl groups, such as a phenylmethyl group, a phenylethyl group, and a diphenylmethyl group.

Among these, alkyl groups are preferable, and primary or secondary alkyl groups are more preferable, as the hydrocarbon groups that can be selected as $R^1$ to $R^4$.

<Antioxidant>

The lubricating oil composition used in one aspect of the invention may contain an antioxidant. The antioxidant may be used alone or in combination of two or more kinds.

In a lubricating oil composition used in one aspect of the present invention, the content of the antioxidant may be suitably determined according to the application, but it is preferably 0.01 to 6.0 mass %, more preferably 0.05 to 4.0 mass %, still more preferably 0.10 to 2.0 mass %, and yet still more preferably 0.30 to 1.5 mass %, relative to the total amount (100 mass %) of the lubricating oil composition.

Examples of an antioxidant used in one aspect of the invention include an amine-based antioxidant, a phenol-based antioxidant, a molybdenum-based antioxidant, a sulfur-based antioxidant, and a phosphorus-based antioxidant.

Among these, the antioxidant used in one aspect of the present invention preferably includes one or more selected from amine-based antioxidants and phenol-based antioxidants, and more preferably includes both of an amine-based antioxidant and a phenolic-based antioxidant.

Examples of amine-based antioxidants include diphenylamine-based antioxidants such as diphenylamine and alkylated diphenylamines having alkyl groups with 3 to 20 carbon atoms; and naphthylamine-based antioxidants such as α-naphthylamine, phenyl-α-naphthylamine, and substituted phenyl-α naphthylamine having alkyl groups with 3 to 20 carbon atoms.

Examples of phenol-based antioxidants include monophenol-based antioxidants such as 2,6-di-t-butylphenol, 2,6-di-t-butyl-4-methylphenol, 2,6-di-t-butyl-4-ethylphenol, isooctyl-3-(3,5-di-t-butyl-4-hydroxyphenyl)propionate, and octadecyl-3-(3,5-di-t-butyl-4-hydroxyphenyl)propionate; diphenol-based antioxidants such as 4,4'-methylenebis(2,6-di-t-butylphenol) and 2,2'-methylenebis(4-ethyl-6-t-butylphenol); and hindered phenol-based antioxidants.

Examples of molybdenum-based antioxidants include molybdenum trioxide and/or a molybdenum-amine complex made by reacting molybdic acid with an amine compound.

Examples of sulfur-based antioxidants include dilauryl-3,3'-thiodipropionate.

Examples of phosphorus-based antioxidants include phosphites.

<Lubricating Oil Additives>

A lubricating oil composition used in one aspect of the present invention may contain lubricating oil additives other than the components mentioned above, according to the application, to the extent that the effects of the present invention are not impaired.

Examples of such lubricating oil additives other than components mentioned above include a pour point depressant, a viscosity index improver, a demulsifier, a friction modifier, a corrosion inhibitor, a metal deactivator, an antistatic agent, and an anti-foaming agent.

Each of these lubricating oil additives may be used alone or may be used in combination of two or more kinds.

The contents of these lubricating oil additives can each be appropriately adjusted such that the effects of the present invention are not impaired, but usually the contents of the additives are each independently 0.001 to 15 mass %, preferably 0.005 to 10 mass %, and more preferably 0.01 to 5 mass %, relative to the total amount (100 mass %) of the lubricating oil composition.

[Method for Using Lubricating Oil Composition and Method for Evaluating Degradation]

The present invention provides a method for using a lubricating oil composition according to [1] below and a method for evaluating degradation of a lubricating oil composition according to [2] below.

[1] A method for using a lubricating oil composition in which the content of a metal-based detergent (X) having a base number of 100 mgKOH/g or less is 630 mass ppm or less in terms of metal atoms and the content of sulfated ash is 1.5 mass % or less, the method comprising a step of measuring a value of at least one physical property among the electrostatic capacity and dielectric constant of the lubricating oil composition while the lubricating oil composition is in use to evaluate the progress of degradation of the lubricating oil composition.

[2] A method for evaluating degradation of a lubricating oil composition in which the content of a metal-based detergent (X) having a base number of 100 mgKOH/g or less is 630 mass ppm or less in terms of metal atoms and the content of sulfated ash is 1.5 mass % or less, the method comprising a step of measuring a value of at least one physical property among the electrostatic capacity and dielectric constant of the lubricating oil composition to evaluate the progress of degradation of the lubricating oil composition.

The lubricating oil composition used in the method of use and the method for evaluating degradation is designed by adjusting the contents of the metal-based detergent (X) and sulfated ash as described above so that the progress of degradation can be accurately determined by measuring the physical property, i.e., electrostatic capacity or dielectric constant.

In addition, the lubricating oil composition used in one aspect of the invention has a property where at least one of the electrostatic capacity and dielectric constant increases with time from the start of use. Therefore, by measuring at least one of the electrostatic capacity and dielectric constant at any point in time or continuously while the lubricating oil composition is in use, and focusing on the changes in the measured value of the physical property, the progress of degradation of the lubricating oil composition can be evaluated in a very convenient manner.

According to the method for using a lubricating oil composition and the method for evaluating degradation of a lubricating oil composition in one aspect of the present invention, there is no particular limitation on the specific technique employed for a method for measuring a value of at least one of the physical properties, i.e., electrostatic capacity and dielectric constant, and for a method for evaluating the progress of degradation of the lubricating oil composition, but, for example, the following techniques can be employed.

<Method for Measuring Physical Properties and Method for Evaluating Progress of Degradation>

As the degradation of a lubricating oil composition progresses, the values of the electrostatic capacity and the dielectric constant of the lubricating oil composition increase. This is because polar substances (mainly polar substances caused by oxidation or thermal degradation, and polar substances mixed into the lubricating oil composition for some reason) are generated by degradation of the lubricating oil composition, and an increase in the amount of such polar substances causes changes in the values of electrostatic capacity and dielectric constant.

After measuring the value of electrostatic capacity or dielectric constant at a given frequency, the "electrostatic capacity ratio" or the "dielectric constant ratio," that is, the ratio of the change in the electrostatic capacity or dielectric constant with respect to the frequency, is calculated. From these values, the progress of degradation of the lubricating oil composition can be evaluated.

The frequency at which the electrostatic capacity or dielectric constant is measured is preferably 1 to 10,000 Hz, more preferably 5 to 5,000 Hz, still more preferably 7 to 1,000 Hz, yet still more preferably 10 to 200 Hz, and particularly preferably 20 to 120 Hz, from the viewpoint of determining the progress of degradation more accurately.

The temperature of the lubricating oil composition when measuring the electrostatic capacity or dielectric constant is preferably 0 to 100° C., more preferably 5 to 80° C., still more preferably 10 to 60° C., and yet still more preferably 15 to 50° C.

For example, when electrostatic capacity of a new oil is $C_1$, electrostatic capacity of a degraded oil is $C_2$, a dielectric constant of the new oil is $\varepsilon_1$, and a dielectric constant of the degraded oil is $\varepsilon_2$ when measured at a given frequency, the "electrostatic capacity ratio" and the "dielectric constant ratio" can be calculated from the following equations (1) and (2), respectively.

$$[\text{Electrostatic capacity ratio}] = C_2/C_1 \qquad \text{Equation (1):}$$

$$[\text{Dielectric constant ratio}] = \varepsilon_2/\varepsilon_1 \qquad \text{Equation (2):}$$

The larger the electrostatic capacity ratio calculated from equation (1) and the larger the value of the dielectric constant ratio calculated from equation (2), the greater the amount of polar substance that may occur in the lubricating oil composition, meaning that the lubricating oil composition is degrading.

[Measurement Apparatus]

The present invention also provides a measurement apparatus for measuring a value of at least one physical property among the electrostatic capacity and dielectric constant of a lubricating oil composition in which the content of a metal-based detergent (X) having a base number of 100 mgKOH/g or less is 630 mass ppm or less in terms of metal atoms and the content of sulfated ash is 1.5 mass % or less.

This measurement apparatus is provided with a measurement unit for measuring the value of the physical property at a predetermined point in time; and a recording section for recording the value of the physical property measured by the measurement unit.

The measurement apparatus in one aspect of the present invention preferably further comprises an evaluation unit for evaluating the progress of degradation of the lubricating oil composition based on the value of the physical property recorded in the recording section.

Figure 1:
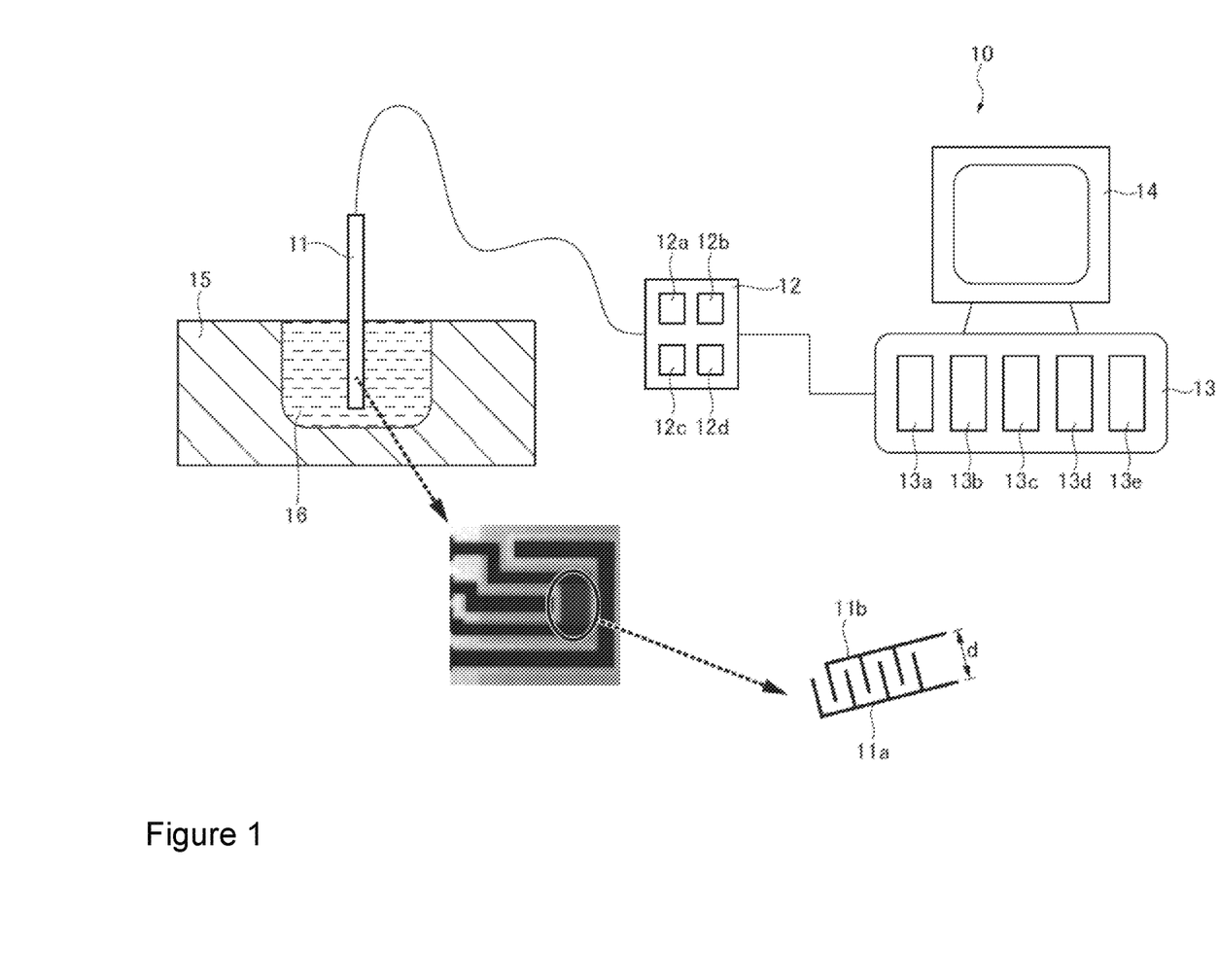
FIG. 1: A schematic view showing an example of an apparatus for measuring the electrostatic capacity or dielectric constant of a lubricating oil composition and the progress of degradation of the lubricating oil composition.

FIG. 1 is a schematic view showing an example of an apparatus in one aspect of the present invention for measuring the electrostatic capacity or dielectric constant of a lubricating oil composition and the progress of degradation of the lubricating oil composition.

A measurement apparatus 10 shown in FIG. 1 is mainly provided with an electrode unit 11, a converter 12, and a computer 13.

The electrode unit 11 preferably has so-called comb-shaped electrodes, as shown in FIG. 1. The comb-shaped electrodes shown in FIG. 1 has a pair of electrodes 11a and 11b. The electrodes 11a and 11b each have a plurality of teeth protruding in a comb shape, and the teeth of electrode 11a and those of electrode 11b are arranged with a predetermined spacing d (preferably 1 to 5 mm, preferably 1 to 3 mm, more preferably 2 to 3 mm).

The converter 12 is mainly provided with, for example, an AC power supply 12a, an ammeter 12b, a voltmeter 12c, and a conversion section 12d. The AC power supply 12a applies an AC voltage of a predetermined frequency to the electrode unit 11. The AC voltage is, for example, a sine wave with an amplitude of ±1.25 V, where its frequency is suitably selected from 20 to 120 Hz. The ammeter 12b and the voltmeter 12c measure the current and voltage passing through the electrode unit 11, respectively. The conversion section 12d converts the current and voltage values, which are obtained as analog signals by the ammeter 12b and voltmeter 12c, respectively, into digital signals and outputs them to the computer 13.

The computer 13 may have, for example, a configuration which is mainly provided with a complex impedance calculating circuit 13a, an electrostatic capacity calculating circuit 13b, a recording section 13c, a dielectric constant calculating section 13d, and an evaluation section 13e, as shown in FIG. 1. The complex impedance calculating circuit 13a calculates the complex impedance using the current and voltage values obtained from the ammeter 12b and the voltmeter 12c, respectively. The electrostatic capacity calculating circuit 13b calculates the electrostatic capacity using the complex impedance. The dielectric constant calculating section 13d calculates the dielectric constant using the electrostatic capacity. The recording section 13c may be, for example, a hard disk, a solid state disk, a memory card, or the like, and records the initial electrostatic capacity and initial dielectric constant of the lubricating oil composition to be measured, i.e., the electrostatic capacity and dielectric constant of the lubricating oil composition that is not yet degraded, and also records the electrostatic capacity calculated by the electrostatic capacity calculating circuit 13b and the dielectric constant calculated by the dielectric constant calculating section 13d. The evaluation section 13e evaluates the progress of degradation of the lubricating oil composition based on the electrostatic capacity and dielectric constant stored in the recording section 13c.

In the measurement apparatus shown in FIG. 1, the electrode unit 11 and converter 12 configure the measurement unit, and the computer 13 configures the recording and evaluation units.

The computer 13 is preferably further connected to a display 14. The display 14 displays changes in the value of at least one of the electrostatic capacity and dielectric constant so that the progress of degradation of the lubricating oil composition can be confirmed.

When the measurement apparatus 10 is installed in an engine or the like, the pair of electrodes 11a and 11b are inserted into a lubricating oil composition 16 that is stored in an oil pan 15 or the like of an automobile or other vehicle in which the engine is mounted. In the examples described below, the measurement apparatus 10 is used together with a heater and a container. The size of the container is large enough to store a lubricating oil composition in an amount of, for example, 5 ml or more, and the heater maintains the temperature of the lubricating oil composition stored in the container at a constant temperature, for example, at 30° C.

A specific procedure for obtaining the values of electrostatic capacity and dielectric constant of a lubricating oil composition and the progress of degradation of the lubricating oil composition using the measurement apparatus 10 will be described. First, the electrode unit 11 is immersed in a lubricating oil composition, and an AC voltage at a predetermined frequency ($H_n$) is applied between the electrodes 11a and 11b by the AC power supply 12a whose frequency can be controlled. Then, the complex impedance calculating circuit 13a calculates the complex impedance of the lubricating oil composition from current I and voltage V measured by the ammeter 12b and the voltmeter 12c and the phase difference between current I and voltage V, and the electrostatic capacity calculating circuit 13b calculates the electrostatic capacity ($C_n$) from the imaginary part (reactance) $Z_C$ of the impedance (which is composed by a real part (resistive component) $Z_R$ and an imaginary part (reactance) $Z_C$) according to the following equation.

$$Z = Z = V/I = Z_R + Z_C = R + 1/j\omega C_n \qquad \text{Equation (I):}$$

(In the equation, Z is the impedance, $Z_R$ is the resistive component of the impedance, $Z_C$ is the imaginary part of the impedance, R is the resistance, j is the imaginary unit, ω is the angular frequency of alternating current, and Cn is the electrostatic capacity.)

Then, if necessary, the dielectric constant ($\varepsilon_n$) is calculated from the value of the electrostatic capacity ($C_n$) by the dielectric constant calculating circuit 13d. The following relationship (II) holds between the dielectric constant ($\varepsilon_n$) and the electrostatic capacity ($C_n$).

$$\varepsilon_n = C_n \times d/s \qquad \text{Equation (II):}$$

(In the above equation, d represents the distance between the electrodes 11a and 11b, and s represents the surface area of the electrodes 11a and 11b.)

The measurement voltage for measuring the electrostatic capacity ($C_n$) is preferably 0.1 to 10 V.

The values of the electrostatic capacity and dielectric constant are recorded in the recording section 13c.

The evaluation section 13e reads the electrostatic capacity and dielectric constant stored in the recording section 13c and evaluates the progress of degradation of the lubricating oil composition. For example, the following techniques can be employed for more detailed evaluation of degradation of a lubricating oil composition, which can be suitably selected according to the application.

A technique in which the lubricating oil composition is judged to have degraded when the ratio of the measured values of electrostatic capacity and dielectric constant to the initial values of electrostatic capacity and dielectric constant is greater than a predetermined value.

A technique in which the lubricating oil composition is judged to have degraded when the difference between the initial values of electrostatic capacity and dielectric constant and the measured values of electrostatic capacity and dielectric constant is greater than a predetermined value.

A technique in which the lubricating oil composition is judged to have degraded when the measured values of electrostatic capacity and dielectric constant exceed the threshold values derived from the initial values of electrostatic capacity and dielectric constant and other factors either beforehand or from time to time.

Figure 2:
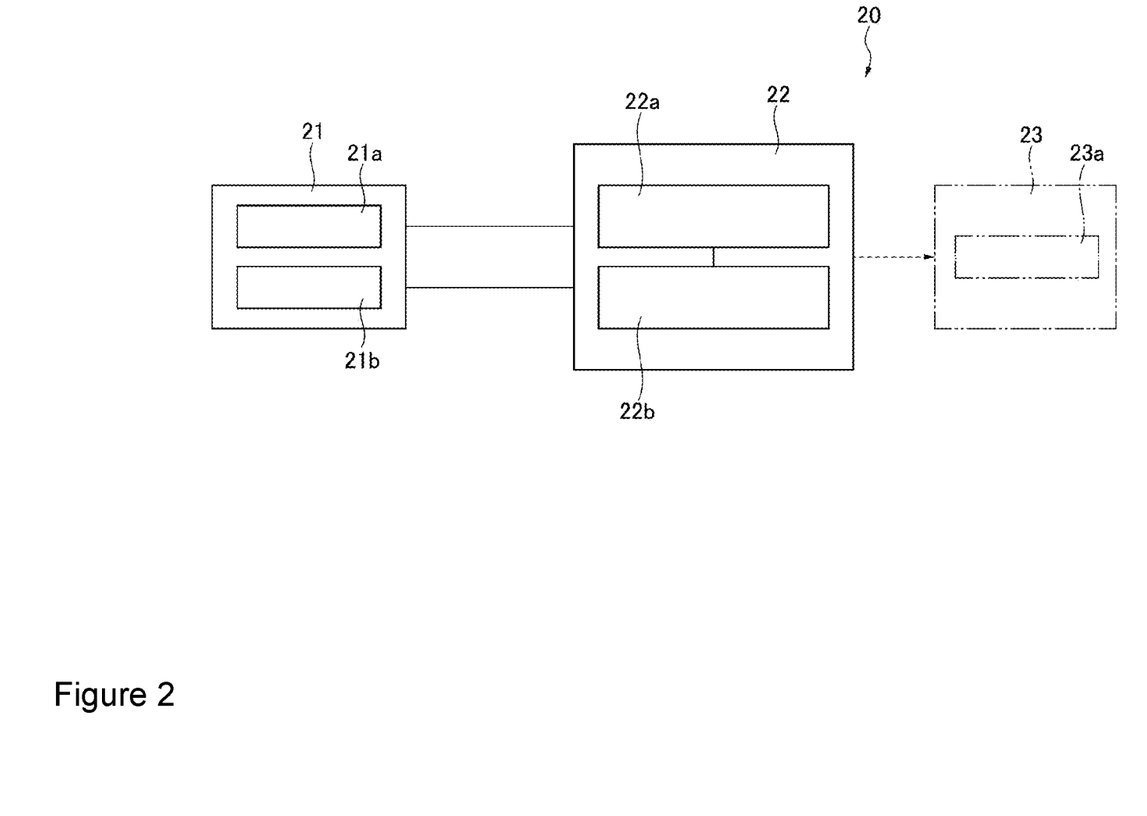
FIG. 2: A schematic view showing another example of an apparatus for measuring the electrostatic capacity or dielectric constant of a lubricating oil composition and the progress of degradation of the lubricating oil composition.

FIG. 2 is a schematic view showing an example of an apparatus in another aspect of the present invention for measuring the electrostatic capacity or dielectric constant of a lubricating oil composition and the progress of degradation of the lubricating oil composition.

A measurement apparatus 20 shown in FIG. 2 is provided with an electrode unit 21, an electrostatic capacity measuring unit 22, and a dielectric constant calculating unit 23.

The electrode unit 21 has a pair of electrodes 21a and 21 facing each other. The electrostatic capacity measuring unit 22 is provided with an AC power supply 22a and an electrostatic capacity measuring circuit 22b. The AC power supply 22a applies an AC voltage of a predetermined frequency between the pair of electrodes 21a and 21b. The electrostatic capacity measuring circuit 22 measures the electrostatic capacity between the pair of electrodes 21a and 21b. The dielectric constant calculating section 23 has a dielectric constant calculating circuit 23a that calculates the dielectric constant based on the value of electrostatic capacity measured by the electrostatic capacity measuring section 22.

A specific procedure for obtaining the values of electrostatic capacity and dielectric constant of a lubricating oil composition and the progress of degradation of the lubricating oil composition using the measurement apparatus 20 will be described.

First, the electrode unit 21 is immersed in a lubricating oil composition, and an AC voltage at a predetermined frequency ($H_n$) is applied between the pair of electrodes 21a and 21 by the AC power supply 22a in the electrostatic capacity measuring unit 22, and the electrostatic capacity measuring circuit 22 measures the electrostatic capacity ($C_n$) between the electrodes 21a and 21b. Then, if necessary, the dielectric constant ($\varepsilon_n$) is calculated from the value of the electrostatic capacity ($C_n$) by the dielectric constant calculating circuit 23a. The dielectric constant ($\varepsilon_n$) is calculated by the above equation (II).

The progress of degradation of the lubricating oil composition is determined by the evaluation section 13e in the same manner as in the embodiment shown in FIG. 1.

A simple measurement apparatus 20 shown in FIG. 2 is sufficiently useful for a method in which the electrostatic capacity ($C_n$) of a lubricating oil composition is directly measured to calculate the dielectric constant ($\varepsilon_n$) of the lubricating oil composition therefrom.

In all of the aspects, the electrode unit 21 preferably comprises comb-type electrodes, and more preferably comb-type microelectrodes. Specifically, if comb-type electrodes are used in the electrode unit 21, the measurement apparatus 20 can be downsized so that only a small amount of sample oil (lubricating oil composition) needs to be collected to measure the values of electrostatic capacity and dielectric constant of the lubricating oil composition to evaluate the progress of degradation of the lubricating oil composition. Therefore, the measurement apparatus 20 can be incorporated into various kinds of equipment that use a lubricating oil composition.

Moreover, an LCR meter or a C-meter can be used as the electrostatic capacity measuring unit 22 and the dielectric constant calculating unit 23.

Similar to the measurement apparatus 10 shown in FIG. 1, the measurement apparatus 20 may be provided with a computer and a display connected to the computer. The computer in the measurement apparatus 20 preferably has the same configuration as the computer 13 in the measurement apparatus 10 shown in FIG. 1.

For example, the computer in the measurement apparatus 20 may be equipped with an evaluation section and may store a table in advance to evaluate the progress of degradation of a lubricating oil composition referring to this table. The table returns a value indicating that the lubricating oil composition is in a degraded state when the ratio of the measured values of electrostatic capacity and dielectric constant, the difference of the measured values of electrostatic capacity and dielectric constant, or the measured values of electrostatic capacity and dielectric constant are specific values. When the evaluation section obtains a value indicating that the lubricating oil composition is in a degraded state from the table, it judges that the lubricating oil composition has degraded and issues a notification or warning. A notification or warning may be given by indication on the display or by other means, such as a sound.

The measurement apparatuses 10 and 20 in one aspect of the present invention can be incorporated as a part of an operation monitoring system for equipment or a device such as an engine, etc., to monitor and evaluate the progress of degradation of the lubricating oil composition at any point in time or continuously. Therefore, the measurement apparatuses 10 and 20 of the present invention can also be used as a degradation monitoring system for a lubricating oil composition in various kinds of equipment and devices.

EXAMPLES

Hereinafter, the present invention will be described more specifically by way of examples, although the present invention should not be limited in any way to these examples. Methods for measuring the various physical properties are as follows.

(1) Kinematic Viscosity and Viscosity Index

The kinematic viscosity and viscosity index were measured and calculated in accordance with JIS K2283:2000.

(2) Contents of Calcium Atoms and Boron Atoms

The contents were measured in accordance with JPI-5S-38-92.

(3) Content of Nitrogen Atoms

The content was measured in accordance with JIS K2609:1998.

(4) Base Number

The base number was determined in accordance with the perchloric acid method or the hydrochloric acid method of JIS K2501:2003.

(5) Content of Sulfated Ash

The content was measured in accordance with JIS K2272:1998.

Examples 1-8 and Comparative Examples 1-2

A base oil and various additives of the kinds shown in Table 1 were added and mixed in the compounding amounts shown in Table 1, thereby preparing each lubricating oil composition.

Details of each component used in the preparation of the lubricating oil composition are as follows.

<Base Oil>
"500N Mineral oil": paraffinic mineral oil classified in Group II, 100° C. kinematic viscosity=10.9 mm$^2$/s, viscosity index=107.

<Metal-Based Detergent>
"Ca salicylate (X-1)": calcium salicylate with base number=80 mgKOH/g (perchloric acid method) and Ca atom content=2.32 mass %.
"Ca sulfonate (X-2)": calcium sulfonate with base number=16.5 mgKOH/g (perchloric acid method) and Ca atom content=2.15 mass %.
"Ca salicylate (Y-1)": calcium salicylate with base number=350 mgKOH/g (perchloric acid method) and Ca atom content=12.1 mass %.

<Ashless Dispersant>
"Non-boron-modified bis-succinimide": polybutenyl bis-succinimide having polybutenyl group of Mw=950 and nitrogen atom content=1.15 mass %.
"Boron-modified mono succinimide": borylation product of polybutenyl monosuccinimide having polybutenyl group of Mw=950, boron atom content (B)=1.9 mass %, nitrogen atom content (N)=1.8 mass %, and B/N=1.06.

<Anti-Wear Agent>
"ZnDTP": zinc dialkyldithiophosphate

<Antioxidant>
"Phenol-based antioxidant"
"Amine-based antioxidant"

<Other Additives>
"Corrosion inhibitor, anti-foaming agent, etc."

A degraded oil was prepared for each of the prepared lubricating oil compositions to determine the base number and the electrostatic capacity ratio by the ISOT test as follows. The results of them are set forth in Table 1.

(1) Preparation of Degraded Oil

In the ISOT test (165.5° C.) in accordance with JIS K2514-1:2013, a test oil (lubricating oil composition) was subjected to forced degradation using copper and iron pieces as catalysts. After 48, 72, and 120 hours, the base numbers of the degraded oil were determined in accordance with the hydrochloric acid method of JIS K2501:2003. The lower the base number, the more the lubricating oil composition has degraded. In Table 1, the ratio of the base number of each degraded oil to the base number of the new oil [degraded oil/new oil] is shown as the base number ratio.

(2) Electrostatic Capacity Ratio

Using the measurement apparatus shown in FIG. 2 for measuring the degree of degradation/alteration of a lubricating oil, which is provided with an electrostatic capacity measuring unit and a dielectric constant calculating unit, the capacitance (electrostatic capacity) at a frequency of 20 Hz was measured for a new oil and degraded oils that had been subjected to forced degradation for specified time by the ISOT test described above (degraded oils obtained after 48, 72, and 120 hours). Table 1 shows the ratio of the electrostatic capacity of each degraded oil to the electrostatic capacity of the new oil at 20 Hz [degraded oil/new oil] as the electrostatic capacity ratio. The conditions for measuring the electrostatic capacity were as follows.

<Measurement Conditions>
Electrodes: Comb-type microelectrodes (electrodes for electrochemical measurement "Comb type electrode Pt", catalog No. 012126, manufactured by BAS Inc.)
Voltage: ±1.25V
Oil quantity: 5 ml
Oil temperature: 30° C.

TABLE 1

| | | | | Example 1 | Example 2 | Example 3 | Example 4 | Example 5 |
|---|---|---|---|---|---|---|---|---|
| Formulation of lubricating oil composition | Base oil | 500N Mineral oil | mass % | 89.80 | 88.35 | 87.70 | 88.25 | 88.80 |
| | Metal-based detergent | Ca salicylate (X-1): 80 mgKOH/g | mass % | — | 1.80 | 2.60 | — | — |
| | | Ca sulfonate (X-2): 16.5 mgKOH/g | mass % | — | — | — | 1.90 | — |
| | | Ca salicylate (Y-1): 350 mgKOH/g | mass % | 2.40 | 2.05 | 1.90 | 2.05 | 2.40 |
| | Ashless dispersant | Non-boron-modified bis-succinimide | mass % | 4.00 | 4.00 | 4.00 | 4.00 | 4.80 |
| | | Boron-modified monosuccinimide | mass % | 1.00 | 1.00 | 1.00 | 1.00 | 1.20 |
| | Anti-wear agent | ZnDTP | mass % | 1.20 | 1.20 | 1.20 | 1.20 | 1.20 |
| | Antioxidant | Phenol-based antioxidant | mass % | 0.50 | 0.50 | 0.50 | 0.50 | 0.50 |
| | | Amine-based antioxidant | mass % | 0.50 | 0.50 | 0.50 | 0.50 | 0.50 |
| | Other additives | Corrosion inhibitor, anti-foaming agent, etc. | mass % | 0.60 | 0.60 | 0.60 | 0.60 | 0.60 |
| | — | Total | mass % | 100.00 | 100.00 | 100.00 | 100.00 | 100.00 |
| Content of metal-based detergent (X) in terms of Ca | | | mass ppm | 0 | 418 | 603 | 409 | 0 |
| Content of metal-based detergent (Y) in terms of Ca | | | mass ppm | 2,904 | 2,481 | 2,299 | 2,481 | 2,904 |
| [Ca of metal-based detergent (X)]/ [Ca of metal-based detergent (Y)] | | | — | 0 | 0.17 | 0.26 | 0.16 | 0 |
| Sum content of metal-based detergents (X) + (Y) in terms of Ca | | | mass ppm | 2,904 | 2,898 | 2,902 | 2,889 | 2,904 |
| Sulfated ash | | | mass % | 1.3 | 1.3 | 1.3 | 1.3 | 1.3 |

TABLE 1-continued

| Physical properties of degraded oil after ISOT test | Base number ratio (hydrochloric acid method) | Degraded oil (ISOT 165.5° C. after 48 hours) | — | 0.19 | 0.31 | 0.33 | 0.16 | 0.21 |
|---|---|---|---|---|---|---|---|---|
| | | Degraded oil (ISOT 165.5° C. after 72 hours) | — | 0.15 | 0.20 | 0.23 | 0.15 | 0.16 |
| | | Degraded oil (ISOT 165.5° C. after 120 hours) | — | 0.12 | 0.14 | 0.17 | 0.13 | 0.13 |
| | Electrostatic capacity ratio | Degraded oil (ISOT 165.5° C. after 48 hours) | — | 0.994 | 1.007 | 1.010 | 0.987 | 0.997 |
| | | Degraded oil (ISOT 165.5° C. after 72 hours) | — | 1.002 | 1.013 | 1.012 | 0.992 | 1.003 |
| | | Degraded oil (ISOT 165.5° C. after 120 hours) | — | 1.011 | 1.019 | 1.015 | 1.005 | 1.015 |

| | | | Example 6 | Example 7 | Example 8 | Comparative example 1 | Comparative example 2 |
|---|---|---|---|---|---|---|---|
| Formulation of lubricating oil composition | Base oil | 500N Mineral oil | 89.30 | 89.20 | 89.00 | 87.40 | 87.20 |
| | Metal-based detergent | Ca salicylate (X-1): 80 mgKOH/g | — | — | — | 3.00 | — |
| | | Ca sulfonate (X-2): 16.5 mgKOH/g | — | — | — | — | — |
| | | Ca salicylate (Y-1): 350 mgKOH/g | 2.40 | 2.40 | 3.20 | 1.80 | 5.00 |
| | Ashless dispersant | Non-boron-modified bis-succinimide | 4.00 | 4.00 | 4.00 | 4.00 | 4.00 |
| | | Boron-modified monosuccinimide | 1.00 | 1.00 | 1.00 | 1.00 | 1.00 |
| | Anti-wear agent | ZnDTP | 1.20 | 1.80 | 1.20 | 1.20 | 1.20 |
| | Antioxidant | Phenol-based antioxidant | 0.75 | 0.50 | 0.50 | 0.50 | 0.50 |
| | | Amine-based antioxidant | 0.75 | 0.50 | 0.50 | 0.50 | 0.50 |
| | Other additives | Corrosion inhibitor, anti-foaming agent, etc. | 0.60 | 0.60 | 0.60 | 0.60 | 0.60 |
| | — | Total | 100.00 | 100.00 | 100.00 | 100.00 | 100.00 |
| | | Content of metal-based detergent (X) in terms of Ca | 0 | 0 | 0 | 696 | 0 |
| | | Content of metal-based detergent (Y) in terms of Ca | 2,904 | 2,904 | 3,872 | 2,178 | 6,050 |
| | | [Ca of metal-based detergent (X)]/ [Ca of metal-based detergent (Y)] | 0 | 0 | 0 | 0.32 | 0.00 |
| | | Sum content of metal-based detergents (X) + (Y) in terms of Ca | 2,904 | 2,904 | 3,872 | 2,874 | 6,050 |
| | | Sulfated ash | 1.3 | 1.3 | 1.5 | 1.3 | 2.3 |
| Physical properties of degraded oil after ISOT test | Base number ratio (hydrochloric acid method) | Degraded oil (ISOT 165.5° C. after 48 hours) | 0.20 | 0.17 | 0.26 | 0.37 | 0.40 |
| | | Degraded oil (ISOT 165.5° C. after 72 hours) | 0.17 | 0.13 | 0.21 | 0.31 | 0.32 |
| | | Degraded oil (ISOT 165.5° C. after 120 hours) | 0.13 | 0.09 | 0.19 | 0.17 | 0.30 |
| | Electrostatic capacity ratio | Degraded oil (ISOT 165.5° C. after 48 hours) | 0.992 | 0.999 | 1.001 | 1.011 | 1.004 |
| | | Degraded oil (ISOT 165.5° C. after 72 hours) | 1.003 | 1.004 | 1.004 | 1.009 | 1.000 |
| | | Degraded oil (ISOT 165.5° C. after 120 hours) | 1.010 | 1.009 | 1.007 | 1.004 | 0.992 |

As can be appreciated from Table 1, for the lubricating oil compositions prepared in Examples 1-8, the base number ratio indicating the progress of degradation decreased while the electrostatic capacity ratios increased along with time of the ISOT test. On the other hand, for the lubricating oil compositions prepared in Comparative examples 1 to 2, in which either the content of the metal-based detergent (X) in terms of metal atoms or the content of the sulfated ash exceeded a predetermined value, the electrostatic capacity ratio decreased as the base number ratio decreased, indicating a discrepancy between the progress of degradation of the lubricating oil composition and the electrostatic capacity ratio.

In each of the examples, the electrostatic capacity of the new oil and degraded oil were measured to evaluate the progress of degradation of the lubricating oil composition from the ratio of the electrostatic capacity of the degraded oil to the electrostatic capacity of the new oil [degraded oil/new oil] (electrostatic capacity ratio). The progress of degradation of the lubricating oil composition can similarly be evaluated by measuring their dielectric constants. Specifically, considering the relationship represented by equation (II) above, it is clear that the above electrostatic capacity ratio is the same value as the ratio of the dielectric constant of the degraded oil to the dielectric constant of the new oil [degraded oil/new oil] (dielectric constant ratio). Therefore, the progress of degradation of the lubricating oil composition can also be confirmed by focusing on the value of the dielectric constant ratio.

DESCRIPTION OF REFERENCE NUMERALS

10 Measurement apparatus
11 Electrode unit

11a Electrode
11b Electrode
12 Converter
12a AC power supply
12b Ammeter
12c Voltmeter
12d Conversion section
13 Computer
13a Complex impedance calculating circuit
13b Electrostatic capacity calculating circuit
13c Recording section
13d Dielectric constant calculating section
13e Evaluation section
14 Display
20 Measurement apparatus
21 Electrode unit
21a Electrode
21b Electrode
22 Electrostatic capacity measuring unit
22a AC power supply
22b Electrostatic capacity measuring circuit
23 Dielectric constant calculating section
23a Dielectric constant calculating circuit

The invention claimed is:

1. A method for using a lubricating oil composition, comprising:
   measuring a value of at least one physical property selected from an electrostatic capacity and a dielectric constant of a lubricating oil composition in use; and
   evaluating a progress of degradation of the lubricating oil composition from the value of at least one physical property selected from the electrostatic capacity and the dielectric constant of the lubricating oil composition,
   wherein a content of a metal-based detergent having a base number of 100 mgKOH/g or less is 630 mass ppm or less in terms of metal atoms in the lubricating oil composition, a content of sulfated ash is 1.5 mass % or less in the lubricating oil composition, and the measuring of the value of at least one physical property comprising measuring the value using at least one comb-type electrode at a single frequency of from 20 Hz to 120 Hz.

2. A method for evaluating degradation of a lubricating oil composition, comprising:
   measuring a value of at least one physical property selected from an electrostatic capacity and a dielectric constant of a lubricating oil composition; and
   evaluating a progress of degradation of the lubricating oil composition from the value of at least one physical property selected from the electrostatic capacity and the dielectric constant of the lubricating oil composition,
   wherein a content of a metal-based detergent having a base number of 100 mgKOH/g or less is 630 mass ppm or less in terms of metal atoms in the lubricating oil composition, a content of sulfated ash is 1.5 mass % or less in the lubricating oil composition, and the measuring of the value of at least one physical property includes measuring the value using at least one comb-type electrode at a single frequency of from 20 Hz to 120 Hz.

3. The method according to claim 2, wherein the measuring includes measuring the value at any point in time or continuously while the lubricating oil composition is in use.

4. A lubricating oil composition, wherein a content of a metal-based detergent having a base number of 100 mgKOH/g or less is 630 mass ppm or less in terms of metal atoms in the lubricating oil composition, a content of sulfated ash is 1.5 mass % or less in the lubricating oil composition, the lubricating oil composition has a degraded state presented by measuring at least one physical property selected from an electrostatic capacity and a dielectric constant thereof, and the measuring of the at least one physical property includes measuring the value using at least one comb-type electrode at a single frequency of from 20 Hz to 120 Hz.

5. The lubricating oil composition according to claim 4, wherein when the lubricating oil composition is continuously used immediately from a start of use, at least one of the electrostatic capacity and the dielectric constant of the lubricating oil composition increases with time from the start of use.

6. An apparatus for measuring a value of at least one physical property selected from an electrostatic capacity and a dielectric constant of the lubricating oil composition of claim 4, comprising:
   a measurement unit comprising circuitry configured to measure a value of the physical property at a predetermined point in time; and
   a recording section comprising circuitry configured to record the value of the physical property measured by the measurement unit,
   wherein the circuitry of the measurement unit includes at least one comb-type electrode.

7. The measurement apparatus according to claim 6, further comprising:
   an evaluation section comprising circuitry configured to evaluate a progress of degradation of the lubricating oil composition based on the value of the physical property recorded in the recording section.

* * * * *